United States Patent

Cooper

[11] Patent Number: 5,570,703
[45] Date of Patent: Nov. 5, 1996

[54] CONTOURED THERAPEUTIC SPINAL SUPPORT

[76] Inventor: Philip L. Cooper, 1700 Elizabeth St., Anniston, Ala. 36207

[21] Appl. No.: 390,308

[22] Filed: Jan. 23, 1995

[51] Int. Cl.$^6$ ..................................... A61F 5/01
[52] U.S. Cl. .................. 128/845; 5/633; 602/19; 606/240
[58] Field of Search .............. 5/630, 633, 652, 5/653; 128/845; 601/136; 602/19, 60, 61; 606/237, 240, 241, 245; 297/284.4, 285, 296

[56] References Cited

U.S. PATENT DOCUMENTS

| | | | |
|---|---|---|---|
| 1,833,426 | 12/1931 | Knudson | 606/240 |
| 2,558,105 | 6/1951 | Schinman | 606/240 X |
| 3,719,185 | 11/1970 | Hanes | 5/630 X |
| 4,230,099 | 10/1980 | Richardson | 606/240 |
| 4,705,030 | 11/1987 | Tepperberg | 606/240 |
| 5,279,310 | 1/1994 | Hsien | 128/845 |

FOREIGN PATENT DOCUMENTS 2549169  5/1976  Germany ................. 128/845

*Primary Examiner*—Richard J. Apley
*Assistant Examiner*—David R. Risley

[57] ABSTRACT

A rounded, pliable, resilient spinal support with straddling contours and defining slopes which gives direct, firm-felt support and massaging therapy to the spine. The round flexing pivot (10) fits between a backrest and the recesses of the user's back, anchored in place by sacral stabilizer (12) and the sacrum. Stabilizer (12) is thin for comfort and allows defining slope (14) to push downward against the sacrum, while the thicker lumbar arch support (16) pushes in against the lumbar region of the back, and defining slope (18) pushes upward against the lower thoracic region of the back. The thin, tapered thoracic stabilizer (20) allows the shoulders to push against the backrest and to anchor my support in place at the upper end. This interrelated pushing encourages the "S"-shape curvature of the spine desired for good posture. As the defining slopes are pushing and the two end stabilizers are being pushed, the straddling contours of spinous process stabilizer (26) and transverse process stabilizers (22) are fitted snugly against the vertebrae. This provides a firm feeling of security so that the muscles can relax, relieving any spasm. It also allows decompression of the vertebral column by giving direct, underneath support. My support also massages the spine. Each unforgiving bone makes a dimple in the three process stabilizers causing a bulging of the support material into the gaps between the bones. This bulging fills the gaps and massages the softer tissue between and among the bones as the user makes any movement.

2 Claims, 1 Drawing Sheet

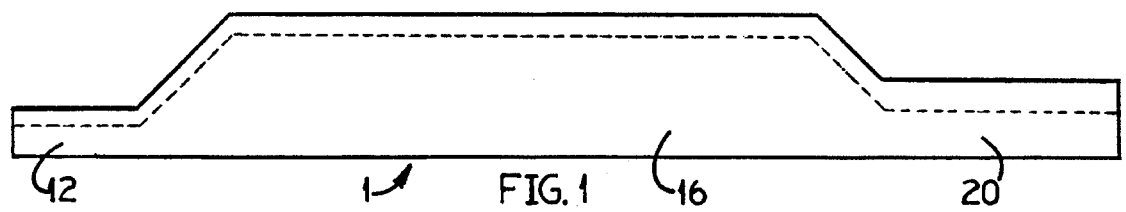
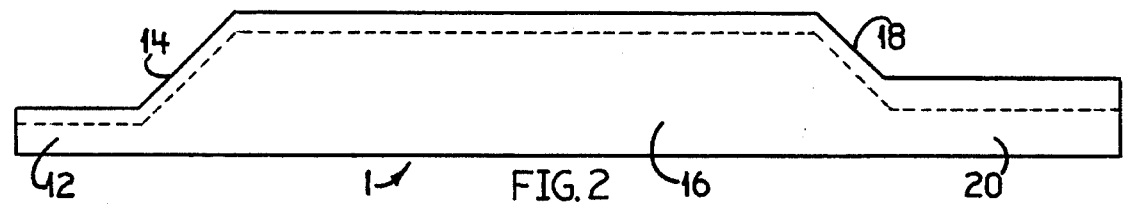
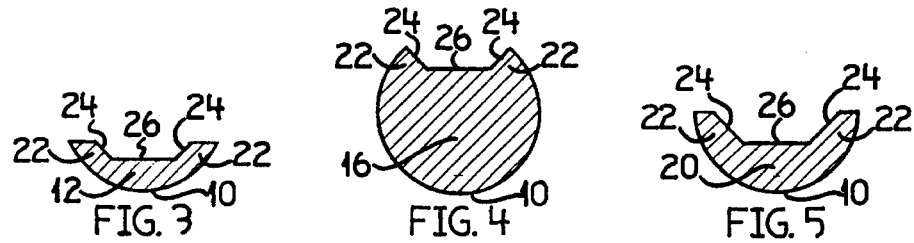
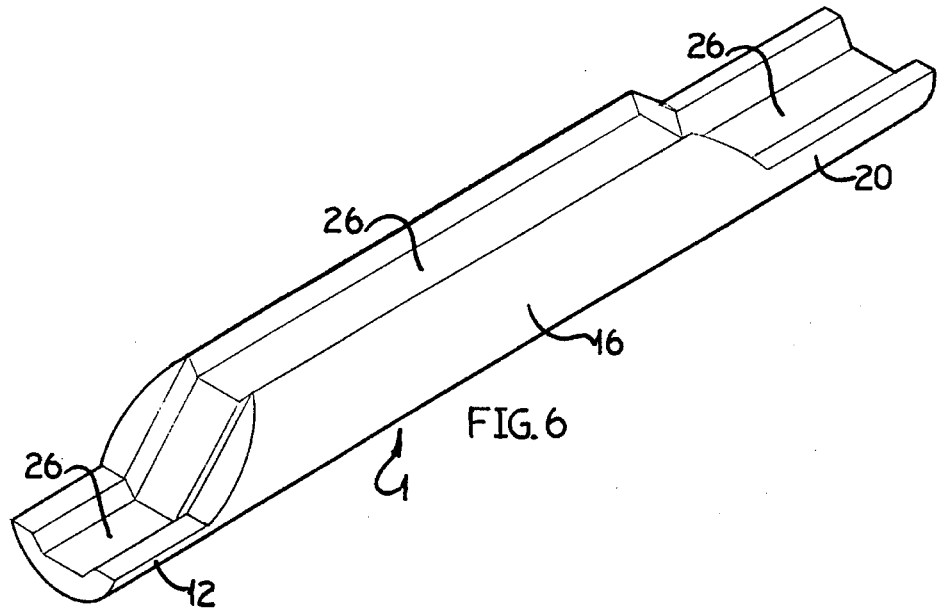

CONTOURED THERAPEUTIC SPINAL SUPPORT

BACKGROUND—FIELD OF INVENTION

This invention relates to medical instruments, specifically to physical therapy.

BACKGROUND—DESCRIPTION OF PRIOR ART

According to medical authorities the vast majority of backaches are often called "non-specific" because they have no obvious cause. There are also no obvious, easy cures. Most non-specific backaches are probably due to a sprained ligament or vertebral joint that causes surrounding muscles to go into painful spasm. In other cases pain is due to straining a muscle or Joint or to emotional tension reflected in the knotting up of back muscles.

These authorities usually recommend lying flat on your back for as long as you can on a bed with a fairly hard orthopedic mattress. This recommendation is generally accepted as the most appropriate treatment. Since this therapy does not always work, we need to look beyond the obvious treatment.

Non-specific backaches are specifically located within the spinal column's vertebrae where they need specific care even when the pain is non-specific. Bed rest doesn't give specific support to the spinal column, because of the placement of the spinal column deep within the back, with the back's surfaces concaving inward toward the spinal column. This concaved placement gives added strength to the back. It also makes it very difficult to get support directly to the vertebral column for relief of pain within the column. Because the outer surfaces of the back make first bodyweight contact on either side of the concaved, recessed placement of the vertebral column with the surface of the bed, the support that the vertebral column gets from the bed is from either side of the vertebral column, not from directly underneath, where the support should be.

Treatment of disorders or injuries with physical methods or agents usually includes one or more of the following: massage, heat treatment (including ultrasound treatment and short-wave diathermy), and exercise. Exercise may be passive.

Physical therapy is used to prevent or reduce joint stiffness and to restore muscle strength in the treatment of arthritis or after a fracture has healed. It is also used to reduce pain, inflammation, and muscle spasm, and to retrain joints and muscles after stroke or nerve injury.

OBJECTS AND ADVANTAGES

The primary object of my contoured therapeutic spinal support is to provide a means of support directly to the spine for the purpose of relieving pain in the back brought on by injury, tension, or other causes. It is also designed to help prevent back injuries by promoting better posture and keeping the muscles around the spine supple by the massaging effect of the support.

The following are among the many advantages of my spinal support.

(a) It is lightweight.

(b) It is easy to use, requiring very little effort to place it against one's back.

(c) It is convenient to use, because it fits between the back and any surface which would normally support the back.

(d) Its smooth surface is designed not to damage anything with which it comes in contact, including clothing or upholstery.

(e) The support directly to the spinal column increases as the body relaxes against the contours of my support.

(f) The massaging effect of my spinal support occurs with each normal body movement as one sits or lies against the support. For example, the muscles surrounding the spine are massaged by my support as the body picks up a glass to take a drink, writes a letter, turns the pages of a book, crosses the legs, or shifts gears.

(g) It provides support directly to the spinal column instead of to the outer (that is, lateral) surfaces of the back.

(h) It provides therapy without having to leave one's home.

(i) It can also provide therapy while traveling, in either a sitting or reclining position.

(j) The stabilizer section of my spinal support is designed to hold the support in place against the backrest of any seat, even if the user leans forward.

Other objects and advantages of my contoured therapeutic spinal support may be seen from the following drawings and description of the operation of the support.

DRAWING FIGURES

FIG. 1 shows side view of my contoured therapeutic spinal support.

FIG. 2 shows side view with numerals.

FIG. 3 shows section view of sacral stabilizer.

FIG. 4 shows section view of lumbar arch support.

FIG. 5 shows section view of thoracic stabilizer.

FIG. 6 shows a perspective view of the contoured therapeutic spinal support.

LIST OF REFERENCE NUMERALS IN DRAWINGS 10 flexing pivot
12 sacral stabilizer
14 defining slope to lumbar arch support
16 lumbar arch support
18 defining slope to thoracic stabilizer
20 thoracic stabilizer
22 transverse process stabilizer
24 transverse process stabilizer tapers
26 spinous process stabilizer

DESCRIPTION OF DRAWINGS—FIGS. 1 TO 5

FIG. 1 shows a side view of my contoured therapeutic spinal support, 1 comprising an elongated cylindrical member the left edge of the drawing being the lower end of the support and right edge being the upper end. The long, smooth surface at the top of FIG. 2 is a rounded, flexing pivot 10. A defining slope 14 connects a sacral stabilizer 12 (the sacral section), shown in detail in FIG. 3, to a lumbar arch support 16 (the lumbar section), shown in detail in FIG. 4. Lumbar arch support 16 is connected by a defining slope 18 to a thoracic stabilizer 20 (the thoracic section), shown in detail in FIG. 5.

FIGS. 3, 4, and 5 show flexing pivot 10, rounded to allow flexing from side to side. These cross sections also show the varying thicknesses of sacral stabilizer 12, lumbar arch support 16, and thoracic stabilizer 20. Spinous process stabilizer 26 is in the form of an elongated notch and is in the center of the side opposite flexing pivot 10. The stabilizer 26 is flanked on either side by a transverse process stabilizer 22 in the form of opposing ridges, and it is connected to each by a transverse process stabilizer taper 24.

OPERATION—FIGS. 2 TO 5

My contoured therapeutic spinal support secures the vertebrae by body pressure and massages the muscles between the bones. The round structure of the support allows it to return to its contoured shape even after being distorted by pressure and flexing. The whole of the spinal support's integral contoured body is interrelated by mutual actions of compression and flexing. With these actions the support becomes an instrument of therapy.

The round unsculptured surface of the instrument as shown in FIG. 2 serves as flexing pivot 10. Recessed in the padding of a soft backrest or stationed against a hard backrest, position sacral stabilizer 12's flat surface against the coccyx and the round surface against the backrest. The support pivots with body movement and grabs the muscles with a firm hold of security as the user reclines against it.

Lumbar arch support 16, the thicker section of the support, pushes upward against the lumbar section of the back. This produces a more desirable "S"-shape curve of the vertebral column as it is when standing and not the slightly bowed position when sitting or reclining without my support.

The slightly bowed position causes the vertebral disks to be compressed, hindering the return of a slipped disk to its original position. The push upward of the support has removed much of the compression. The compression now is against the lower part of the vertebrae, causing a slight pinching effect. This pinching effect is similar to the method used by orthodontists in positioning the teeth, little by little.

My contoured therapeutic spinal support allows the user to feel not only support from the bed or backrest, but also to feel the firm underneath support directly to the vertebral column, especially in the lumbar region.

The first priority after an injury to the vertebral column is to stabilize it. This priority is valid not only after an injury, but with any pain in the vertebral column. The strained muscles that are in a spasm will, because of unstable movements of the vertebrae, cause a reflex arc stimuli which causes contractions and recontractions of the muscles. This causes continuation of the spasm. This is the time when the muscles are most painful and will remain painful until you can grab these muscles with a firm hold of security. Then the muscles will begin to relax, because of the feeling of security. Spinous process stabilizer 26 and transverse process stabilizers 22 as shown in the cross sections of FIGS. 3, 4, and 5 provide this firm hold of security.

Along the length of my support, first body-weight contact is made with transverse process stabilizers 22. These fit snugly against either side of the vertebrae. As the body feels this support, it relaxes further against my spinal support until it makes contact with spinous process stabilizer 26. At this point each vertebra is surrounded on three sides by my support. As pressure from the body pushes the vertebrae further against the support and into the stabilizers, the support is felt even more firmly allowing the muscles to continue relaxing until the tension is removed from these muscles.

The thickness in thoracic stabilizer 20 has been reduced because of the rib cage. The need for uplift here is less, but defining slope 18 does push upward against the ribs toward the sternum forcing the shoulders back against the backrest or bed. This action helps prevent slumping of the shoulders and the bowing that can occur in the upper back.

CONCLUSION, RAMIFICATIONS, AND SCOPE OF INVENTION

Thus, the reader will see that my contoured therapeutic spinal support is a means of physical therapy directed to the spinal column. It provides comfortable service for persons in their leisure or working hours, wherever there is a backrest or a place to recline.

It stabilizes the vertebrae as it massages the soft tissue surrounding the vertebral column.

The embodiment shown is a complete unit. It is lightweight, portable, convenient, and effective. Other embodiments are also possible—my support can be incorporated into various articles. It can be used in the backrests of any vehicular seat or piece of furniture with a backrest. It could also be incorporated into mattresses, mattress pads, stretchers, gurneys, or any similar device. It can be incorporated into items which support, protect, strengthen, or massage the back.

My contoured therapeutic spinal support can be made in various sizes. It can also be made of various materials of either natural or synthetic base having the properties of pliability, elasticity, and resilience. The spinous and transverse process stabilizers could also be tubing filled with gas or liquid.

Although the description above contains many specificities, these should not be construed as limiting the scope of the invention, but as merely providing illustrations of some of the presently preferred embodiments of this invention. Thus, the scope of the invention should be determined by the appended claims and their legal equivalents, rather than by the examples given.

I claim:

1. A spinal support for supporting and massaging the human spine while recumbent or seated, comprising:

a resilient elongated cylindrical member having a sacral section, a lumbar section, and a thoracic section, said lumbar section intermediate said sacral and said thoracic sections, said elongated cylindrical member having an elongated notch extending along the entire length of said elongated cylindrical member defining opposing ridges along either side of said elongated notch, said elongated notch being deeper along said sacral and said thoracic section than said lumbar section such that said lumbar section has a substantially larger cross-section than that of said sacral and said thoracic sections, whereby said elongated cylindrical member may conform to the contours of the sacral, lumbar, and thoracic portions of the human spine, said member grasping the spine and said ridges massaging the muscles adjacent the sides of the spine.

2. The spinal support of claim 1 wherein said elongated notch is beveled on each side to an angle of approximately 45 degrees.

\* \* \* \* \*